US006397102B1

(12) United States Patent
Neuberger

(10) Patent No.: US 6,397,102 B1
(45) Date of Patent: May 28, 2002

(54) DEVICE AND METHOD FOR PHOTOACTIVATED DRUG THERAPY

(75) Inventor: Wolfgang Neuberger, F.T. Labuan (MY)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/611,136

(22) Filed: Jul. 6, 2000

(51) Int. Cl.[7] ............................. A61N 1/30; A01N 41/10
(52) U.S. Cl. ......................................... 604/20; 514/709
(58) Field of Search .............. 604/19–20; 514/709–711, 514/729–738

(56) References Cited

U.S. PATENT DOCUMENTS

| | | | |
|---|---|---|---|
| 5,277,913 A | | 1/1994 | Thompson et al. |
| 5,482,719 A | | 1/1996 | Guillet et al. |
| 5,561,026 A | | 10/1996 | Aoki |
| 5,567,687 A | * | 10/1996 | Magda et al. .................. 514/44 |
| 5,888,997 A | * | 3/1999 | Sessler et al. ............... 514/185 |
| 5,969,111 A | * | 10/1999 | Sessler et al. ................. 534/15 |
| 5,994,410 A | * | 11/1999 | Chiang et al. ............... 514/709 |

* cited by examiner

Primary Examiner—Sharon Kennedy
(74) Attorney, Agent, or Firm—B J Associates; Bolesh J. Skutnik

(57) ABSTRACT

A device and method are presented wherein a common drug for a particular treatment is given to the patient in an inactive form. The drug can be administered systemically or topically. The activity of the drug is regulated by photoactivatible fullerene molecules to which the drug is complexed. When the drug is encapsulated in or attached to the photoactivatible fullerene molecule, it is inactive. However, when the inactive drug complex is subjected to selective irradiation, the complex is broken and the drug is released in an active form. Treatment can be administered over a wide range of body areas, both internally and externally. The selectivity allows the drug in non-treatment areas to remain inactive, and then be removed or passed harmlessly from the body. The present invention facilitates drug treatment administration by allowing very specific treatment while minimizing the side effects.

6 Claims, 5 Drawing Sheets

DEVICE AND METHOD FOR PHOTOACTIVATED DRUG THERAPY

BACKGROUND OF THE INVENTION

1. Field of the Invention

The invention relates generally to photodynamic therapy and in particular to selective photoactivation of a commonly used drug.

2. Invention Disclosure Statement

Drug treatments are used in the treatment of a variety of illnesses. The problem with conventional treatments is their lack of selectivity. Drugs administered systemically are active in areas of the body where treatment is not needed. As a result, negative effects of the drug can be present in those areas. Side effects and their suppression have become an important aspect of developing useful and successful drugs. Drug delivery systems that allow selective activation of a drug only in the areas where the drug's activity is needed would therefore be beneficial.

For example, U.S. Pat. No. 5,482,719 describes a drug delivery system in which a drug is combined with a photosensitive element. In this form, the drug is inactive. However, once the photosensitive element is cleaved off, by irradiation, the drug is released in an active form for treatment. The invention however, has limitations. For example, the drug compound described is complexed with a photosensitive macromolecule. The dimensions of this complex prevent it from migrating throughout the body. Therefore, wherever the complex is administered it will remain there localized for the duration of the treatment. This implies that for a given treatment, the practitioner must separately administer the complex to each area requiring treatment. This process is time consuming and becomes less practical with a greater number of treatment sites. What is needed is an activatible drug complex that has high selectivity yet can migrate throughout many areas of the body.

U.S. Pat. No. 5,277,913 describes a drug delivery system in which the drug is encapsulated in a liposome. Through irradiation or pH changes, the liposome 'membrane' is ruptured and the drug contents released. The system providing for the drug delivery and release is complex and therefore problems can arise with its consistency of response. First, the release of the drug is triggered by irradiation or pH changes that effect a photosensitizer. The photosensitizer in turn produces a compound that will cleave a specific entity in the liposome 'membrane'. As a result, the 'membrane' opens and the liposome contents are allowed to 'spill' from the cavity. Having an indirect pathway to 'membrane' cleavage and drug dispersal leads to a variable and inconsistent treatment. Second, although the drug-release can be initiated through irradiation, the delivery system is also temperature and pH dependant. Both of these factors can vary depending on the part of the body receiving treatment. Therefore where multiple sites are involved, different sites may receive different drug doses for the same treatment. Further at temperatures lower than normal body temperature (37° C.), the percentage of drug release by the liposomes decreases to the point where at 15° C. the release drops to below 15%. This effect makes the invention inapplicable to topical drug applications where skin surface and surrounding environmental temperatures are often too low for an effective release.

Several patents exist that describe the use of photoactivatible fullerene compounds for various applications. Fullerenes are unique spherical structures formed from a specific number of carbon atoms (the number of carbon atoms can vary, in a fixed pattern, depending on the type of fullerene formed). A photosensitive or photoresponsive element can be added directly to the fullerene structure to make it responsive to applications of radiation. When radiation is applied to a 'photosensitized' fullerene, it causes the fullerene structure to change and as a result 'breaks open' the spherical arrangement.

U.S. Pat. No. 5,561,026 as representative of a group of patents describing photoactivation and fullerenes, discloses an invention whereby a photosensitive group is added to the fullerene molecule to 'photosensitive' it. The invention disclosed however describes photoactivatible fullerenes for use as part of an overall photoactivatible or photosensitive material. The invention pertains solely to fullerene molecules used in aggregate comprising a layer or a coating of photosensitive materials. The invention does not suggest or imply using a photoactivatible fullerene as a delivery 'vehicle'.

The present invention relates to using a photoactivatible fullerene as a delivery vehicle to selectively deliver drugs to a treatment site.

BRIEF SUMMARY OF THE INVENTION

It is an aim of the present invention to provide a system for the activation of commonly used drugs with laser radiation whereby the drug compound is selectively activated only in the areas requiring treatment, thereby preventing exposure of non-treatment areas to potentially harmful side effects of the drug.

It is another aim of the present invention to complex the desired drug with a photoactivatible compound such as a 'photosensitized' fullerene such that separation of the drug from the activation complex will activate the drug.

It is a further aim of the present invention to encapsulate the drug in a photoactivatible fullerene cage such that specifically applied radiation will alter the fullerene structure and release the drug.

Still another aim of the present invention is to attach a photoactivatible fullerene molecule to a commonly used drug such that the photoactivatible component of the fullerene molecule is bonded to the drug, and when irradiated will release the drug and thereby activate it.

Yet another aim of the present invention is to have a non-activated drug compound remain inactive and to be harmlessly removed or passed from the body.

Briefly stated, a device and method are presented wherein a common drug for a particular treatment is given to the patient in an inactive form. The drug can be administered systemically or topically. The activity of the drug is regulated by photoactivatible fullerene molecules to which the drug is complexed. When the drug is encapsulated in or attached to the photoactivatible fullerene molecule, it is inactive. When the inactive drug complex is subjected to selective irradiation however, the complex is broken and the drug is released in an active form. Treatment can be administered over a wide range of body areas, both internally and externally. The selectivity allows the drug in non-treatment areas to remain inactive, and then be removed or passed harmlessly from the body. The present invention facilitates drug treatment administration by allowing very specific treatment while minimizing the side effects.

The above, and other objects, features and advantages of the present invention will become apparent from the following description read in conjunction with the accompanying drawings.

DISCLOSURE OF PREFERRED EMBODIMENTS

Drug delivery systems that allow selective activation of a drug only in the areas where the drug's activity is needed are therefore beneficial. Such selective activation may be achieved through photoactivation. In this manner, a drug can be administered to a patient in an inactive form. Radiation can then selectively be applied to the areas requiring treatment. The radiation will serve to 'activate' the drug only in those specific locations. Any inactive drug compound remaining can then be removed or passed harmlessly from the body.

A classic drug for use in a drug treatment regime can be complexed with a photoactivatible fullerene molecule such that when in complex with the fullerene, the drug is in an inactive form. Once the drug-fullerene complex is exposed to selective radiation however, the drug is released from the complex in an active form. This advantage allows practitioners to administer the drug to a patient either systemically or topically over a large area. Irradiation application can be restricted to only those areas that require treatment. Therefore, multiple applications of a drug to different treatment areas, or unnecessary treatment are eliminated. Excess amounts of the drug compound present in non-treatment areas, remain inactive and are easily and harmlessly removed or passed from the body. Practitioners using the system can selectively administer treatment effectively and efficiently to the areas where treatment is required and prevent unnecessary treatment where it is not needed.

Figure 1:
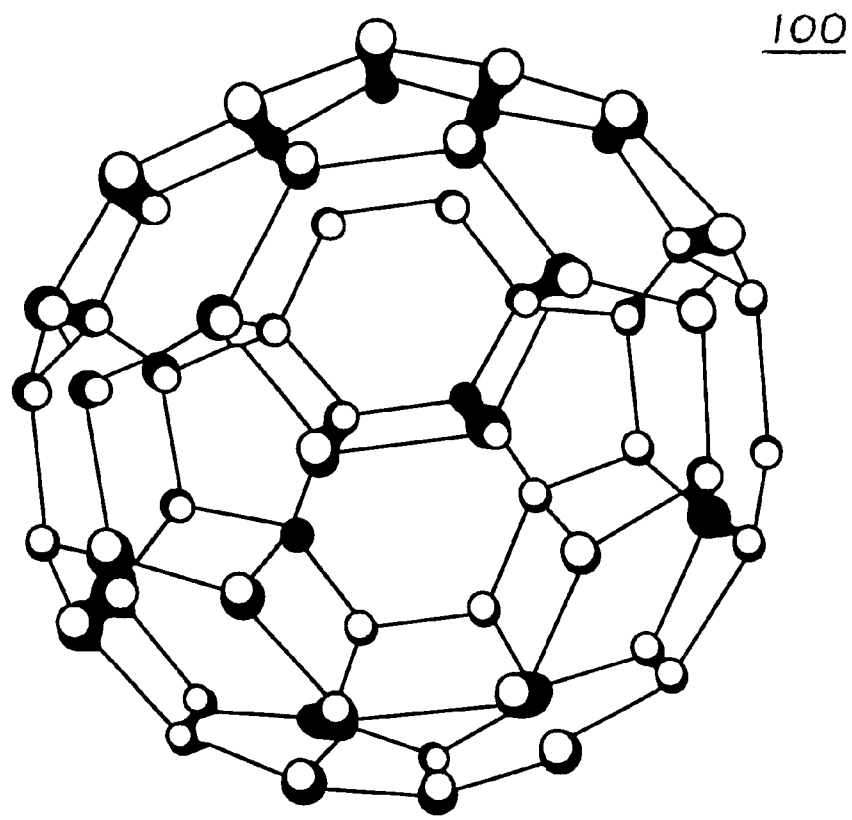
FIG. 1 shows a molecular diagram of a fullerene molecule.

FIG. 1 shows a molecular representation of a fullerene molecule 100. The particular version depicted has 60 carbon atoms ($C_{60}$) arranged in a spherical form. The arrangement of the molecule gives the compound unique optical properties. Variations of the fullerene structure have been shown to exist wherein the number of carbon atoms changes according to a set pattern.

Figure 2:
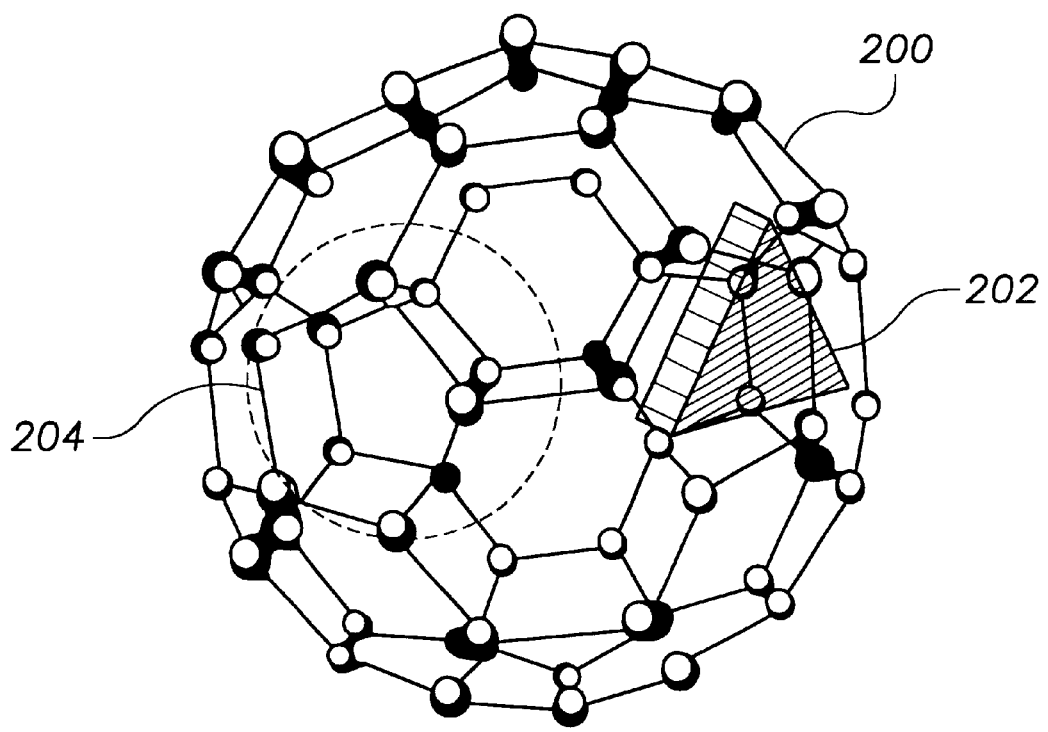
FIG. 2 shows a drug compound encapsulated in a photoactivatible fullerene molecule.

FIG. 2 shows drug compound 204 encapsulated in fullerene molecule 200. In this embodiment, photosensitive compound 202 has been incorporated into the spherical structure of fullerene molecule 200. Drug compound 204 is encased inside fullerene sphere 200 and thus the drug is kept in an inactive form. Fullerene molecule 200 containing drug compound 204 is administered to a patient either systemically or topically. Subsequent selective irradiation of the administered complex in the appropriate treatment areas, with the proper wavelength will cause photosensitive compound 202 to react. Activation of photosensitive compound 202 results in the disruption of the spherical structure of fullerene 200. As a result, fullerene 200 'breaks open', releasing drug 204 in its active form.

Figure 3A:
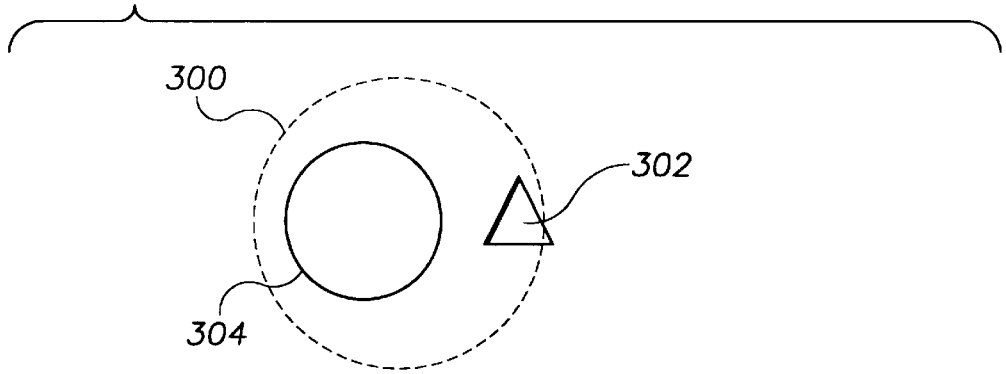
FIG. 3a shows a drug encapsulated in a fullerene.
Figure 3B:
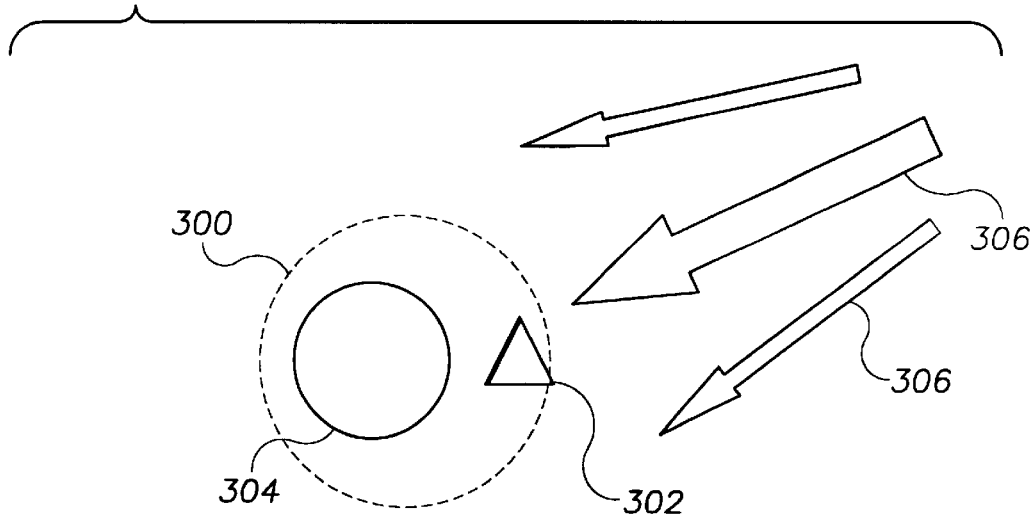
FIG. 3b shows laser energy being administered to a treatment site having a drug encapsulated in a fullerene.
Figure 3C:
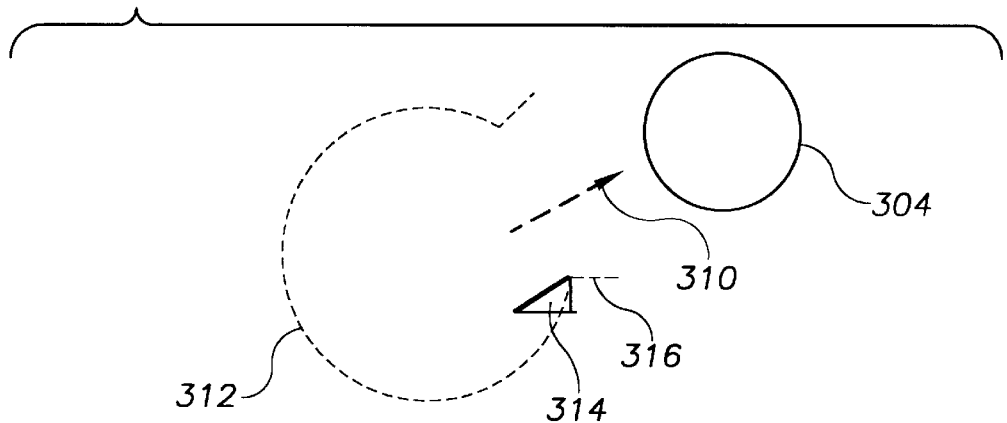
FIG. 3c shows a fullerene with a disrupted spherical structure.

FIG. 3 shows a stepwise depiction of photoactivated drug release. FIG. 3 shows drug 304 encapsulated in fullerene 300. Fullerene 300 has in its structure photosensitive compound 302 that 'responds' to specific wavelengths of radiation. Drug 304 is inactive when encapsulated in fullerene 300. FIG. 3b shows laser energy of the proper 'activation' wavelength 306 being administered at the treatment site. In the path of laser energy 306 is drug 304 encapsulated in fullerene 300. Within the structure of fullerene 300 is photosensitive compound 302. Laser energy 306 will effect photosensitive compound 302 by changing its conformation and will thereby break the spherical structure of fullerene 300. FIG. 3c shows fullerene 312 with disrupted spherical structure 316. The integrity of fullerene 312 is breached when the conformation of photosensitive compound 314 changes in response to applied radiation (see FIG. 3b). As a result, drug 304 is emitted from fullerene 312 as displayed by directional arrow 310. Drug 304, released from fullerene 312 is now in an active form free to treat the surrounding area.

Figure 4:
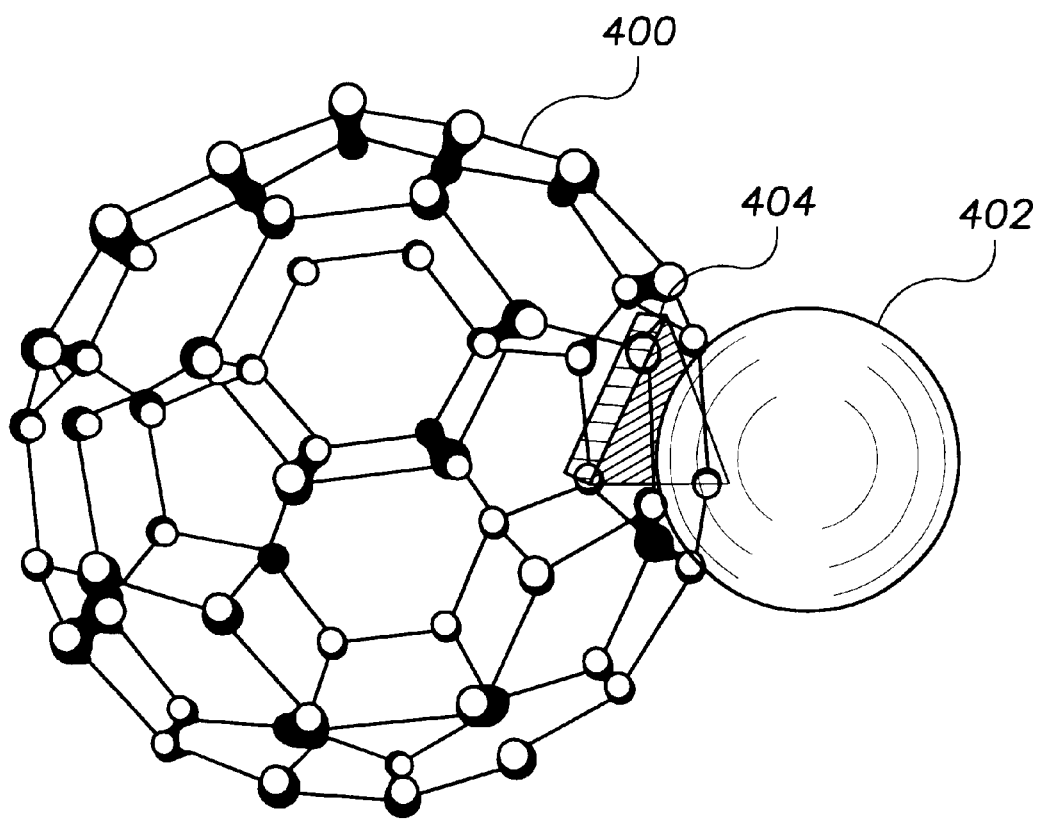
FIG. 4 shows a drug compound attached to a photoactivatible fullerene molecule.

FIG. 4 shows another construction of the drug delivery system according to this invention. Drug compound 402 complexed with photoactivatible fullerene 400. Specifically, drug compound 402 is attached to photosensitive compound 404 that is incorporated in the spherical structure of fullerene molecule 400. In this orientation, drug compound 402 is in an inactive form because the active components of drug compound 402 are attached to photosensitive compound 404. When the complex is irradiated, the conformation of photosensitive compound 404 will change, releasing drug compound 402 in an active form.

Figure 5:
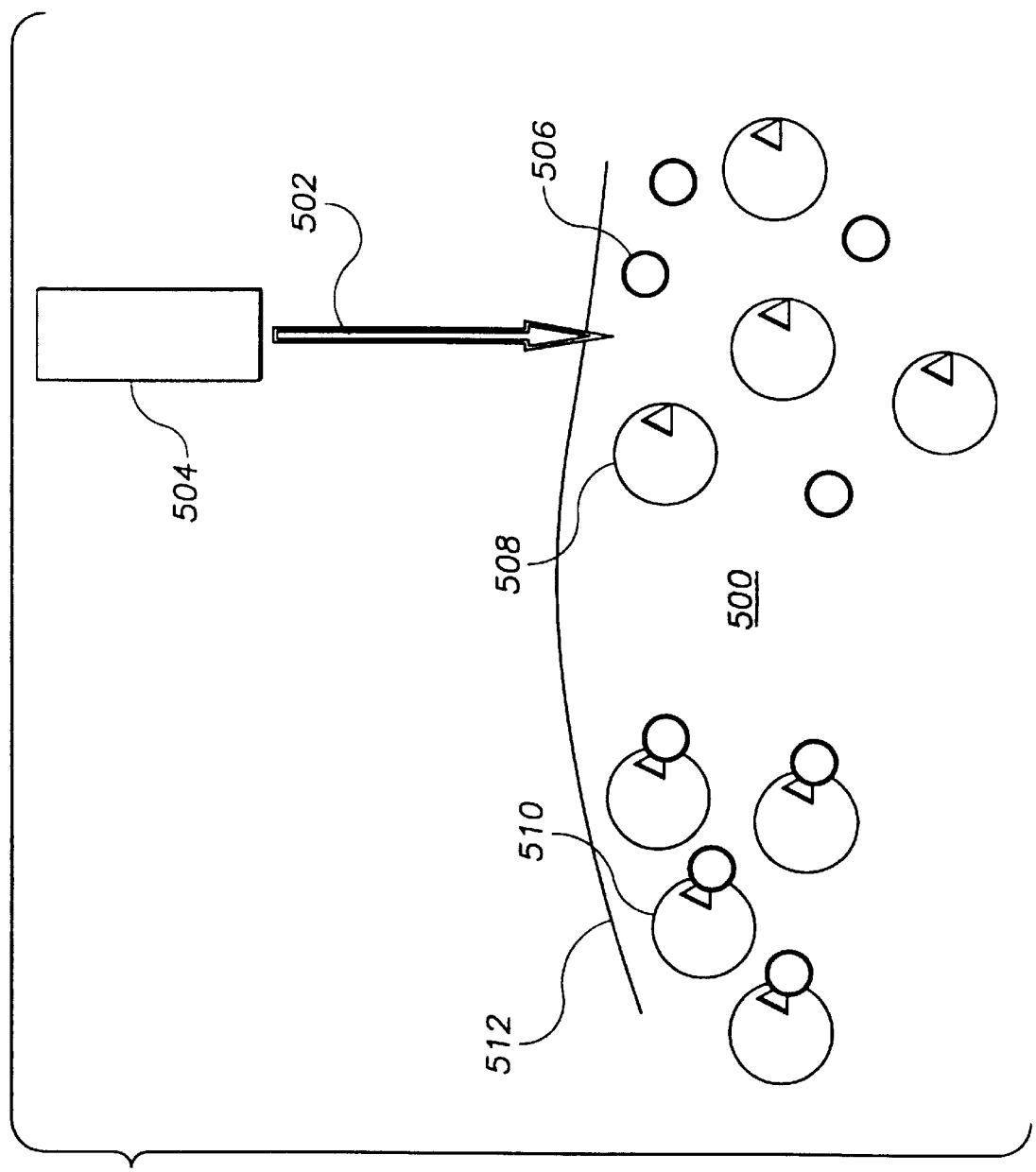
FIG. 5 illustrates how treatment using the system is administered.

FIG. 5 illustrates how treatment is provided. This embodiment shows treatment site 500 where drug complex has been administered systemically. Radiation 502 produced by laser source 504 is projected onto skin surface 512 above treatment site 500. Radiation 502 converts inactive drug complex (drug coupled with photoactivatible fullerene molecule, see FIG. 3) 510 into active drug complex 506 and fullerene molecule 508. This embodiment illustrates how active drug 506 can be released into an area requiring treatment, and that inactive drug complex 510 remains inactive in non-treatment areas.

Having described preferred embodiments of the invention with reference to the accompanying drawings, it is to be understood that the invention is not limited to the precise embodiments, and that various changes and modifications may be effected therein by one skilled in the art without departing from the scope or spirit of the invention as defined in the appended claims.

What is claimed is:

1. A photoactivatible drug delivery system comprising:

a photoactivatible fullerene molecule containing a photosensitive element within its structure; and a drug compound is complexed with said photoactivatible fullerene molecule.

2. A photoactivatible drug delivery system according to claim 1, wherein said drug compound is bound to said photosensitive element on said photoactivatible fullerene molecule such that an active component of said common drug compound is blocked by said fullerene in order to prevent activity of said drug compound.

3. A photoactivatible drug delivery system according to claim 1, wherein said drug compound is encapsulated within said photoactivatible fullerene molecule such that said encapsulated drug compound is inactive.

4. A method for photoactivatible targeted drug delivery comprising the steps of:

administering to a patient a photoactivatible drug complex based on a photoactivatible fullerene molecule;

directing laser radiation, produced by a laser source emitting at an appropriate activation wavelength, at a treatment site;

activating said drug complex by affecting said photosensitive element within said photoactivatible fullerene molecule that in turn causes release of said drug compound in an active form; and allowing said photoactivatible drug complex outside said treatment site to exit said patient while said complex remains inactive.

5. A method of photoactivatible drug delivery according to claim 4, wherein said drug complex is administered systemically to said patient.

6. A method of photoactivatible drug delivery according to claim 4, wherein said drug complex is administered topically to said patient.

* * * * *